United States Patent [19]

Felix et al.

[11] Patent Number: 4,649,131

[45] Date of Patent: * Mar. 10, 1987

[54] GROWTH HORMONE RELEASING FACTOR ANALOGS

[75] Inventors: Arthur M. Felix, West Caldwell; Edgar P. Heimer, Sparta; Thomas F. Mowles, Pine Brook, all of N.J.

[73] Assignee: Hoffmann-La Roche Inc., Nutley, N.J.

[*] Notice: The portion of the term of this patent subsequent to Nov. 11, 2003 has been disclaimed.

[21] Appl. No.: 762,891

[22] Filed: Aug. 6, 1985

Related U.S. Application Data

[63] Continuation-in-part of Ser. No. 653,163, Sep. 24, 1984.

[51] Int. Cl.[4] .................... A61K 37/36; A61K 37/24; C07K 7/10
[52] U.S. Cl. ....................................... 514/12; 514/13; 530/324; 530/325
[58] Field of Search .................................. 514/12, 13; 260/112.5 R; 530/324, 325

[56] References Cited

U.S. PATENT DOCUMENTS 4,529,595 7/1985 Rivier et al. ........................... 514/12
4,562,175 12/1985 Chang et al. .......................... 514/12

FOREIGN PATENT DOCUMENTS 0138416 2/1984 European Pat. Off. .............. 514/12
0117034 10/1984 European Pat. Off. ..... 260/112.5 R

OTHER PUBLICATIONS

Hruby, V. J. and D. H. Rich, editors, Peptides Structure and Function, pp. 853–856 (198), Pierce Chemical Co., Rockford, Ill.
Ling, et al., Biochemical and Biophysical Research Communications, 123:854–861, 1984.
Rivier, et al, Letters to Nature, 300:276–278; 1982.
Guillemin, et al., Science, 218:585–587; 1982.

*Primary Examiner*—Delbert R. Phillips
*Attorney, Agent, or Firm*—Jon S. Saxe; Bernard S. Leon; George M. Gould

[57] ABSTRACT

Novel growth hormone releasing factor analogs in which glycine at position 15 is replaced by appropriately selected amino acids demonstrate enhanced potency for the release of growth hormone and the analogs can be administered to a subject having a deficiency of growth hormone.

37 Claims, No Drawings

GROWTH HORMONE RELEASING FACTOR ANALOGS

This is a continuation-in-part application of Ser. No. 653,163 filed Sept. 24, 1984.

BACKGROUND OF THE INVENTION

Growth hormone releasing factor (GRF) has recently been isolated from human islet cell tumor and structurally characterized by Dr. Guillemin and co-workers at the Salk Institute. Science 218, 585–587 (Nov. 5, 1982). The isolation and characterization of GRF while sought for decades was previously unsuccessful due to its presence in very small quantities. Human hypothalamic growth hormone releasing factor (hGRF) has now been found to have the same structure as GRF isolated from islet cell tumor. Bohlen et al. *Biochem. and Biophys. Res. Comm.*, 114(3) 930–936 (1983)

Rivier and coworkers, Nature 300, 276–278(1982) have described the structure of GRF (1–44) and GRF (1–40), respectively, and shown that GRF is specific for the release of growth hormone. These two forms of GRF are identical at the amino ($NH_2$—) terminal but differ in the termination point of the carboxy (COOH) terminus. GRF (1–44) is further distinguished in having an amide group at the carboxy terminus.

Rivier and Vale et al., Id. have shown that the biological activity of GRF resides in the $NH_2$-terminal portion of the molecule and full intrinsic activity and potency was demonstrated with GRF(1–29)-$NH_2$ in vitro.

Lance et al., Biochemical and Biophysical Research Communications 119(1), 265–272 (1984) have shown that GRF (1–29)-$NH_2$ with substitutions of selected amino acids at positions 1, 2 and 3 cause enhanced release of growth hormone (GH) in both pig and rat in vivo. Rivier, J. E. F. et al. in U.S. Pat. No. 4,518,586 disclose various GRF synthetic peptides including the substitution of D-Ala at position 15. Similarly in U.S. Pat. No. 4,528,190 issued July 9, 1985 also discloses various GRF analogs including the substitution of D-Ala at position 15.

Growth in animals is presumably regulated by a cascade of bio-regulatory molecules. The hypothalamus produces GRF which induces pituitary release of growth hormone. Small quantities of GRF have been found to cause substantial pituitary release of growth hormone into the blood. Thus, GRF has great therapeutic utility in those instances where growth hormone is indicated. For example, GRF may be used in the treatment of hypopituitary dwarfism, diabetes due to growth hormone production abnormalities, promotion of wound healing, treatment of burns and retardation of the aging process. Similarly GRF has utility in the agricultural field. Examples of agricultural uses include, enhanced meat production of fowl or animals raised for food such as pigs, cattle or the like to permit earlier marketing or to produce larger animals for similar time on feed or improve the lean to fat ratios. GRF may also stimulate milk production in dairy cows and egg production in chickens.

SUMMARY OF THE INVENTION

The present invention relates to novel peptides of the formula:

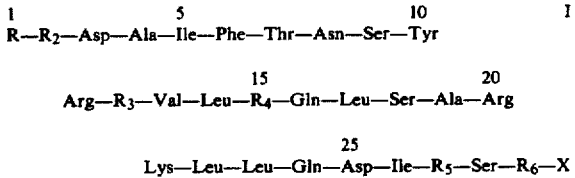

wherein R represents Tyr, D-Tyr, des$NH_2$-Tyr, Ac-Tyr or His; $R_2$ represents Ala N-Methyl-D-Ala or D-Ala; $R_3$ represents Lys or Ala; $R_4$ represents Ala, Leu, Val, Ile, Nle, Nval, $\beta$-Ala or $\alpha$-Aib; $R_5$ represents Met, Leu, Nle, or Ile; $R_6$ represents an amino acid sequence selected from Arg-Gln-Gln-Gly-Glu-Ser-Asn-Gln-Glu-Arg-Gly-Ala-Arg-Ala-Arg-Leu or fragments thereof where the fragment is reduced in number by one to fifteen amino acids from the carboxyl end; and, X is either OH or $NH_2$ and, the pharmaceutically acceptable acid or base addition salts thereof.

Pharmaceutical compositions in accordance with the invention include such analogs which are between twenty-nine (29) and forty-four (44) residues in length dispersed in a pharmaceutical or veterinary acceptable liquid or solid carrier. Such pharmaceutical compositions can be used in clinical medicine, both human and veterinary, for administration for therapeutic and/or diagnostic purposes. Moreover they can be used to promote the growth of warm and cold-blooded animals.

The peptides of this invention are useful in methods for stimulating the release of growth hormone from the pituitary for use in the treatments described above.

DETAILED DESCRIPTION OF THE INVENTION

As used herein, the term "GRF" means human growth hormone releasing factor, a polypeptide having the amino acid sequence (*Science*, 218, 585, Nov. 5, 1982)

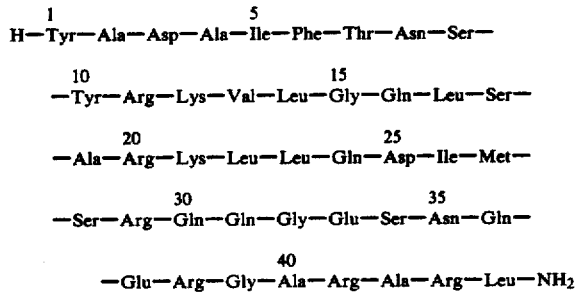

or biologically active fragments having at least the first 29 amino acids of the full polypeptide and displaying growth hormone releasing activity. In accordance with conventional representation, the amino group at the N-terminus appears to the left and the carboxyl group at the C-terminus to the right. Amino acid is taken to mean one of the naturally occurring amino acids typically found in proteins comprising Gly, Ala, Val, Leu, Ile, Ser, Thr, Lys, Arg, Asp, Asn, Glu, Gln, Cys, Met, Phe, Tyr, Pro, Trp and His. Nle means norleucine and Nval means norvaline. Where the amino acid residue has isomeric forms it is the L-form of the amino acid that is represented unless otherwise expressly indicated. The suffixes "-OH" and "-$NH_2$" following "GRF" refer to the free acid and amide forms of the polypeptide, respectively. In the event neither suffix is used, the expression is intended to encompass both forms. Analogs of GRF are indicated by setting forth the substituted amino acid in parentheses before "GRF"; that is, for example, "(Ala$^{15}$)-GRF" indicates a polypeptide having an amino acid sequence corresponding to GRF in which an alanine residue has been substituted for glycine at position 15. Numbers in parentheses following "GRF" indicate fragments of the full polypeptide by giving the position numbers of the amino acid residues, e.g. GRF(1-29) indicates a fragment having the first 29 amino acids of the full sequence.

This invention is based on the discovery that the glycine residue at position 15 of the GRF molecule can be replaced by a different appropriately selected amino acid producing a GRF analog having enhanced biological potency by stimulating the release of growth hormone from the pituitary. Amino acids substituted at position 15 may be selected from the group of hydrophobic amino acids such as Ala, Leu, Val, Ile, Nle and Nval. Alpha-aminoisobutyric acid (α-Aib) an unnatural α-amino acid and Beta-Alanine (β-Ala), an unnatural β-amino acid may also be substituted at position 15. More particularly the GRF analogs having the hydrophobic amino acids such as alanine, valine or leucine substituted at position 15 have been shown to have enhanced biological activity in effecting the release of growth hormone from the pituitary.

Various methods well known in the art may be used to select a particular amino acid for substitution in GRF at a particular position. One such method is to select a substitute amino acid so as to modify the secondary structure or alter the amphiphilic character of the resulting polypeptide as demonstrated by helicity and hydropathicity analysis and further by reducing ease of proteolytic breakdown of the resulting polypeptide. Helicity and hydropathicity analyses are done by conventional methods known in the art.

Further substitutions of appropriately selected amino acids at position 15 in GRF fragments varying in length from about 29 amino acids to less than 44 amino acids were also shown to have enhanced biological activity by increasing pituitary GH release. More particularly substitutions of appropriately selected amino acids at position 15 of GRF (1-29) was shown to have enhanced biological activity.

Additional substitutions of appropriately selected amino acids at other selected positions of the GRF molecule concomitant to the substitution at the 15 position producing a multisubstituted GRF analog yielded peptides having biological potency in effecting the release of GH by the pituitary. Selected positions of the GRF peptide for a second substitution include, but are not limited to, the 1,2 or 12 or 27 position. Selected amino acids for substitution at the appropriately selected positions include tyrosine, des-NH$_2$-tyrosine, Ac-tyrosine, histidine, lysine, alanine, β-alanine and the D-amino acids of the described amino acids. Substitutions at each of the selected positions in addition to the substitution at position 15 may yield a disubstituted, trisubstituted or tetrasubstituted polypeptide.

Further the acid or amide of the full length GRF (1-44), the 29 amino acid GRF (1-29) or a GRF greater than about 29 amino acids and less than 44 amino acids in length in addition to the substitution at the 15 position were found to have enhanced biological activity. Particularly the GRF (1-44) and the GRF (1-29) acid and amide with an appropriately selected amino acid substituted at the 15 position was shown to have enhanced biological activity.

Representative compounds of the present invention include:

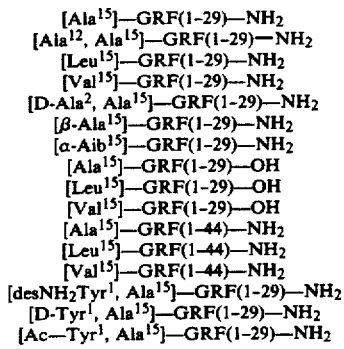

Although the modifications described are for the sequence comprising human growth hormone releasing factor, hGRF, similar modifications may be made to; porcine growth hormone releasing factor, pGRF; bovine growth hormone releasing factor, bGRF; ovine growth hormone releasing factor, oGRF; and caprine growth hormone releasing factor, cGRF.

The polypeptides of this invention can be prepared by solid phase peptide synthesis techniques, solution phase peptide synthesis or by recombinant DNA methods. The newly developed recombinant DNA technique may be used to prepare a portion of an analog containing only naturally occurring amino acid residues, which could then be coupled to a short N-terminal peptide.

Peptides may be prepared using solid phase synthesis, such as that described by Merrifield, *J. Am. Chem. Soc.*, 85, 2149 (1963) although other equivalent chemical syntheses known to one of ordinary skill may be used. Solid phase synthesis is commenced from the C-terminal end of the peptide by coupling a protected amio acid to a suitable resin. A starting material can be prepared by attaching an amino-protected amino acid via a benzyl ester linkage to a chloromethylated resin or a hydroxymethyl resin or via an amide bond to a benzhydrylamine (BHA) resin or methylbenzhydrylamine (MBHA) resin. The resins are available commercially and their preparation is known by one of ordinary skill in the art.

The acid form of the novel analogs may be prepared by the solid phase peptide synthesis procedure using a benzyl ester resin as a solid support. The polypeptide may be purified by preparative high performance liquid chromatography (HPLC) and then shown to be homogeneous by two analytical HPLC systems, isoelectric focusing and high voltage thin layer electrophoresis. Amino acid analysis may be performed so as to confirm the expected amino acid composition. The corresponding amides may be produced by using benzhydrylamine or methylbenzhydrylamine resin as the solid support for solid phase peptide synthesis. Those skilled in the art will recognize that when the BHA of MBHA resin is used, treatment with anhydrous HF to remove the polypeptide from the solid support results in a polypeptide having a terminal amide group.

The C-terminal amino acid e.g. Arg is protected at the Nα-amino and side chain guanidino positions by appropriately selected protecting groups, in the case of Arg by t-butyloxycarbonyl (Boc) and p-toluenesulfonyl (Tos), respectively. The Boc-Arg (Tos)-OH can be first coupled to the benzhydrylamine resin using dicyclohexylcarbodiimide at about 25° C. for 2 hours with stirring. Following the coupling of the Boc protected amino acid to the resin support, the α-amino protecting group is removed, using trifluoroacetic acid (TFA) in methylene chloride or TFA alone. The deprotection is carried out at a temperature between about 0° C. and room temperature.

After removal of the α-amino protecting group, the remaining Boc-protected amino acids are coupled stepwise in the desired order or as an alternative to adding each amino acid separately in the synthesis, some may be coupled to one another prior to addition to the solid phase synthesizer. The selection of an appropriate coupling reagent is known to one of ordinary skill in the art. Particularly suitable is dicyclohexylcarbodiimide (DCC).

Each protected amino acid or amino acid sequence is introduced into the solid phase reactor in excess, and the coupling may be carried out in a medium of dimethylformamide (DMF) or methylene chloride ($CH_2Cl_2$) or mixtures thereof. In cases where incomplete coupling occurs, the coupling procedure is repeated before removal of the Nα-amino protecting group prior to the coupling of the next amino acid. The success of the coupling reaction at each stage of synthesis may be monitored. A preferred method of monitoring the synthesis is by the ninhydrin reaction. The coupling reactions can be performed automatically, as on a Vega 250 Peptide Synthesizer.

Cleavage of the peptide from the resin can be effected using procedures well known in peptide chemistry. Reaction with hydrogen fluoride in the presence of p-cresol and dimethylsulfide at 0° for 1 hour may be followed by a second reaction with hydrogen fluoride in the presence of p-cresol for 2 hours at 0°.

Purification of the polypeptides of the invention can be effected using procedures well known in peptide chemistry. As previously indicated, the subject polypeptides may be purified using preparative HPLC; however, other known chromatographic procedures such as gel permeation, ion exchange and partition chromatography or countercurrent distribution can also be employed.

The polypeptides of this invention have growth hormone releasing activity. Pharmaceutical compositions in accordance with the invention include analogs of about 29 to 44 amino acids in length, or a nontoxic salt of any of these, dispersed in a pharmaceutically or veterinarily acceptable liquid or solid carrier. Such pharmaceutical compositions can be used for therapeutic or diagnostic purposes in clinical medicine, both human and veterinary. For example, they are useful in the treatment of growth-related disorders such as hypopituitary dwarfism and diabetes resulting from abnormalities in growth hormone production. Furthermore, they can also be used to stimulate the growth or enhance feed efficiency of animals raised for meat production, to enhance milk production and stimulate egg production.

Appropriate dosages of the polypeptides of the invention to be administered will vary somewhat depending on the individual subject and the condition being treated. The skilled worker will be able to determine appropriate dosages based on the known circulating levels of growth hormone associated with normal growth and the growth hormone releasing activity of the polypeptide.

Compounds of this invention induced release of growth hormone in vitro five (5) fold greater than that of GRF(1–44). Thus these analogs can be administered in significantly lower dosages than if growth hormone releasing factor were given for the same purpose. As is well known in the art treatment of growth-related disorders will necessitate varying dosages from individual to individual depending upon the degree of insufficiency of growth hormone production. Generally, a dosage range of from 0.04 µg/kg/day to about 1.0 µg/kg/day based on body weight of the subject may be used to stimulate release of growth hormone. The dosages employed to stimulate growth activity in livestock will be significantly higher (per kg. of subject weight) than the dosages employed to restore normal growth in cases of growth hormone deficiencies such as pituitary dwarfism in humans. In livestock generally a dosage in the range of from 0.4 µg/kg/day to about 10 µg/kg/day subcutaneously may be used to stimulate release of pituitary growth hormone.

Thus, there is provided in accordance with this invention a method of treating growth-related disorders characterized by insufficient production of growth hormone which comprises administering an amount of the analogs of this invention sufficient to stimulate the production of growth hormone to levels associated with normal growth.

Normal levels of growth hormone vary considerably among individuals and, for any given individual, levels of circulating growth hormone vary considerably during the course of a day. In adult humans, normal serum levels of growth hormone have been reported to vary from about 0–10 nanograms/ml. In children, normal serum levels of growth hormone have been reported to vary from about 0–20 nanograms/ml.

In order to treat hypopituitary dwarfism effectively with the described analogs, treatment is administered during the period of normal growth. In females, this period generally does not extend far beyond the onset of menses. Thus, treatment of females should be effected approximately from the age of 12 to 16 years, depending upon the individual. In males, the stimulation of growth may be possible for a considerably longer period of time beyond puberty. Thus, effective treatment of males will normally be possible up to about 18 to 19 years of age and, in some individual cases, up to about 25 years.

There is also provided a method of increasing the growth rate of animals by administering an amount of the analog sufficient to stimulate the production of growth hormone at a level greater than that associated with normal growth.

The polypeptides of the invention can be administered in the form of human or veterinary pharmaceutical compositions which can be prepared by conventional pharmaceutical formulation techniques. Compositions suitable for oral, intravenous, subcutaneous, intramuscular, intraperitoneal or intranasal administration may be employed. A suitable dosage form for pharmaceutical use is from about 0.01 to about 0.5 mg of the compound of the invention, which may be lyophilized for reconstitution with sterile water or saline. The composition should be maintained at a pH below about 8.0 in order to maintain the stability of the analog. Serum albumin from the species being treated (e.g. human serum albumin in the case of humans, bovine serum albumin in the case of cows and so forth) may also be present together with other known pharmaceutical adjuvants.

The following examples are presented in order to illustrate the practice of this invention and are not to be construed as limiting the scope of the invention in any way. Unless otherwise stated, all parts and percents are given by weight and all temperatures are in degrees centigrade.

In the examples, optically active protected amino acids in the L-configuration were employed except where specifically noted. The protected amino acids were examined by thin layer chromatography on silica gel G plates and developed with chlorine-TDM. Melting points were determined on a Thomas-Hoover apparatus (uncorrected) and optical rotation was measured in a jacketed 1-dm cell on a Perkin-Elmer Model 141 Polarimeter and conformed to the accepted values. Amino acid analysis was performed on a Waters Amino Acid Analyzer.

The following abbreviations are used in the examples to indicate various protecting groups and reagents.
BOC = t-butyloxycarbonyl
Z = benzyloxycarbonyl
2ClZ = B 2-chlorobenzyloxycarbonyl
Bzl = benzyl
2,6-$Cl_2$-Bzl = 2,6-dichlorobenzyl
Tos = p-toluenesulfonyl
DCC = dicyclohexylcarbodiimide
BHA = benzhydrylamine
DMF = dimethylformamide
TFA = trifluoroacetic acid
$CH_2CL_2$ = methylene chloride
TGA = thioglycolic acid The analogs of this invention were prepared by sequential coupling of amino acids using a commercially available automated solid phase peptide synthesizer (Vega 250 Peptide Synthesizer). Nα-Boc-amino acids were used in the synthesis.

Trifunctional amino acids were protected as Nα-Boc-Lys(2ClZ), Nα-Boc-Asp(OBzl), Nα-Boc-Glu(OBzl), Nα-Boc-Ser(Bzl), Nα-Boc-Thr(Bzl), Nα-Boc-Tyr(2,6-$Cl_2$-Bzl) and Nα-Boc-Arg(Tos).

EXAMPLE 1

Preparation of Boc-Arg(Tos)-Benzhydrylamine-resin

Benzhydrylamine-resin (BHA) (40.44 g, 0.5 mmol/g, 20.22 mmol) was coupled with Boc-Arg(Tos)-OH (34.6 g, 80.7 mmol) in 25% dimethylformamide:methylene chloride [DMF-$CH_2Cl_2$] (250 ml) with DCC (16.78 g, 81.4 mmol) for 2 hours followed by the addition of 1% diisopropylethylamine and reacted for 0.5 hour longer. The resultant Boc-Arg(Tos)-BHA-resin was washed with $CH_2Cl_2$ (3×250 ml), MeOH (3×250 ml), $CH_2Cl_2$ (3×250 ml) and dried. The coupling and washing procedures were repeated and an aliquot was hydrolyzed (1 ml of 6M propionic/HCl at 130° for 2 hours). Amino acid analysis showed a substitution of 0.35 mmol of Arg per gram of resin. The remaining amino groups were acetylated with $Ac_2O$-pyridine yield: 48.88 g.

EXAMPLE 2

Preparation of [Ala$^{15}$]-hGRF (1–29)-benzhydrylamine-resin

Boc-Arg(Tos)-BHA-resin, as prepared in Example 1, (15.0 g, 5.25 mmol) was charged into the reaction vessel of a Vega 250 Peptide Synthesizer and solid phase synthesis performed by the symmetric anhydride procedure for a total of 6 cycles to give hGRF(23–29)-BHA-resin (21.74 g). A 2.5 g (0.60 mmol) portion was removed and subjected to 10 more cycles of solid phase synthesis to give hGRF(13–29)-BHA-resin (2.61 g). A 1.3 g (0.30 mmol) portion was subjected to solid phase synthesis for the remaining 12 cycles. At the end of the synthesis the Boc-group of the N-terminal amino acid residue was removed (TFA) and the peptide-resin, [Ala$^{15}$]-hGRF (1–29)-BHA-resin was dried to give 1.66 g.

EXAMPLE 3

Preparation, purification and characterization of [Ala$^{15}$]-hGRF(1–29)-$NH_2$ The [Ala$^{15}$]-hGRF(1–29)-benzhydrylamine-resin, as prepared in Example 2, (1.66 g) was treated with anhydrous liquid HF using the modified conditions of Tam et al.; Tetrahedron Lett. 23, 2939–2942 (1982); p-cresol (10%): dimethylsulfide (65):HF(25) [total volume: 20 ml] at 0° for 1 hour and evaporated. This was followed by another reaction with p-cresol (10%):HF (90%) [total volume: 20 ml] at 0° C. for 2 hour. The HF was evaporated at 0° (high-vac, CaO trap) and the crude peptide and resin mixture triturated with EtOAc, extracted with TFA, evaporated and the residue triturated with ether and dried. The crude material (1.01 g) was dissolved in 10 ml of $H_2O$ (containing 0.5% TFA), filtered (0.45μ type HA Millipore filter) and loaded onto a Whatman Partisil M-20 ODS-3 column (2×50 cm). The column was eluted (6 mL/min) with a solvent system consisting of $CH_3CN$ (containing 0.25% TFA) and $H_2O$ (containing 0.50% TFA) in a linear gradient mode from 10 to 32% $CH_3CN$ in 120 minutes and held at 32% for an additional 60 minutes. The column was then eluted with a linear gradient going from 32% $CH_3CN$ (0.25% TFA)-$H_2O$ (0.5% TFA) to 38% $CH_3CN$ (0.25% TFA)-$H_2O$ (0.5% TFA) in 90 minutes. The flow rate was continued at 6 mL/min. fractions collected (2 min/fraction) and aliquots analyzed by the analytical HPLC system. The product emerged in fractions 136–140 (252–270 min) which were combined, evaporated and lyophilized to give pure [Ala$^{15}$] GRF(1–29)-$NH_2$, yield: 71.3 mg, 7.05%. Fractions before and after the center cut were combined, evaporated and lyophilized to give 53 mg of semi-pure product which was not processed further.

The product was shown to be homogeneous by analytical HPLC; high voltage thin layer electrophoresis, ($R_{Arg}$=0.33). Tryptic peptide mapping, by analytical HPLC, was similar to that of GRF(1–29)-$NH_2$ with slightly different retention times for the tryptic fragments encompassing residues 12–20 and 13–20 as expected. Amino acid analysis (6N HCl containing 1% thioglycolic acid; 110°; 24 hours): Asp, 3.30; Thr, 1.07; Ser, 2.85; Glu, 2.10; Ala, 3.82; Val, 0.90; Met, 0.98; Ile, 1.87; Leu, 4.11; Tyr, 1.97; Phe, 0.90; Lys, 2.02; Arg. 3.12.

EXAMPLE 4

Preparation of [Ala$^{12,15}$]hGRF(1–29)-BHA-resin

Boc-Arg(Tos)-BHA-resin, of example 1 (5g, 1.75 mmol), was subjected to 4 cycles of solid phase peptide synthesis (as in example 2) to give 6.1 g of protected hGRF (25–29)-BHA-resin. A 2 g portion was removed and subjected to 24 more cycles of solid phase synthesis. The Boc group of the N-terminal amino acid residue was removed (TFA) and the side-chain protected peptide resin [Ala$^{12,15}$]hGRF (1–29)-BHA-resin was dried to give 2.34 g.

EXAMPLE 5

Preparation, Purification and Characterization of [Ala$^{12,15}$]-hGRF(1–29)-NH$_2$ The [Ala$^{12,15}$]hGRF(1–29)-BHA-resin, of example 4 (2.34 g) was treated with anhydrous liquid HF (as in example 3) and 1.15 g of crude [Ala$^{12,15}$]-hGRF(1–29)-NH$_2$ was obtained. The crude product was subjected to HPLC purification (as in example 3) and the desired product emerged in fractions 138–141 which were combined, evaporated and lyophilized, yield: 56 mg of [Ala$^{12,15}$]-hGRF(1–29)NH$_2$ which was shown to be homogeneous by analytical hplc. Amino acid composition (Hydrolysis: 6N HCl-thioglycolic acid; 110°; 24 h): Asp, 3.18; Thr, 0.99; Ser, 2.81; Glu, 2.17; Ala, 5.18; Val, 0.92; Met, 1.05; Ile, 1.92; Leu, 4.27; Tyr, 2.07; Phe, 0.92; Lys, 1.04; Arg, 3.20.

EXAMPLE 6

Preparation of [Leu$^{15}$]hGRF(1–29)-NH$_2$

The remaining 4.1 g of hGRF(25–29)-BHA-resin from example 4 was subjected to 9 cycles of solid phase peptide synthesis to give 6.0 g (1.14 mmoles) of protected hGRF(16–29)-BHA-resin. A portion (1.5 g, 0.28 mmol) was further subjected to 15 cycles of solid phase synthesis, treated with TFA and dried to give 0.98 g of crude side-chain protected [Leu$^{15}$]hGRF(1–29)-BHA-resin. After HF cleavage (as in example 3) and subsequent work-up, 536 mg of crude [Leu$^{15}$]hGRF(1–29)-NH$_2$ was obtained. A 200 mg portion of this material was dissolved in 10 mL of 0.025% TFA (H$_2$O), filtered and loaded onto dual (in series) Synchropak columns (RP-P, 1×25 cm) and the columns were eluted (2 mL/min) with a solvent system consisting of CH$_3$CN (containing 0.025% TFA) and H$_2$O (containing 0.025% TFA) in a linear gradient mode from 25 to 40% CH$_3$CN in 120 min. Fractions (2 min/fraction) were collected and aliquots analyzed by the analytical HPLC system and the product emerged in fractions 24–26 which were combined, evaporated and lyophilized. Yield; 9.9 mg, the product, [Leu$^{15}$]hGRF(1–29)-NH$_2$ was shown to be homogeneous by analytical HPLC. Amino acid composition (Hydrolysis: 6NHCl-TGA; 110°; 24 h); Asp, 3.01; Thr, 0.96; Ser, 2.82; Glu, 2.09, Ala, 3.10; Val, 0.99; Met, 1.02; Ile, 1.91; Leu, 5.19; Tyr, 1.93; Phe, 0.92; Lys, 1.98; Arg, 3.07.

EXAMPLE 7

Preparation of [Val$^{15}$]-hGRF(1–29)-NH$_2$

Protected hGRF(16–29)-BHA-resin (1.5 g, 0.28 mmol), from example 6, was subjected to 15 cycles of solid phase peptide synthesis, treated with TFA and dried to give 1.3 g of side chain protect [Val$^{15}$]-hGRF(1–29)-BHA-resin. Anhydrous HF cleavage (as in example 3) and subsequent work-up gave 625 mg of crude [Val$^{15}$]hGRF (1–29)-NH$_2$. A 200 mg portion was subjected to HPLC purification (as in example 6) and 7.0 mg of purified [Val$^{15}$]hGRF(1–29)-NH$_2$ was obtained. The product was shown to be homogeneous by analytical HPLC. Amino acid composition (Hydrolysis: 6NHCl-TGA; 110°; 24 h): Asp, 2.99; Thr, 0.97; Ser, 2.78; Glu, 2.09; Ala, 3.07; Val;, 1.98; Met, 0.97; Ile, 1.93; Leu, 4.16; Tyr, 2.02; Phe, 0.96; Lys, 1.99; Arg, 3.08.

EXAMPLE 8

Preparation of [D-Ala$^2$, Ala$^{15}$]hGRF(1–29)-NH$_2$

Protected hGRF(16–29)-BHA-resin (3 g 0.57 mmol), from example 6, was subjected to 13 cycles of solid phase peptide synthesis to give 3.6 of protected [Ala$^{15}$]-hGRF(3–29)-BHA-resin. A portion (1 g, 0.16 mmol) was subjected to 2 cycles of solid phase synthesis and treated with TFA to give 1.02 g of [D-Ala$^2$, Ala$^{15}$]-hGRF(1–29)-BHA-resin. Cleavage from the resin with anhydrous HF, as in example 3 and subsequent work-up gave 575 mg of crude [D-Ala$^2$,Ala$^{15}$]hGRF(1–29)-NH$_2$.

A 200 mg portion was subjected to HPLC purification (as in example 6) and 18.3 mg of purified [D-Ala$^2$,Ala$^{15}$]-hGRF(1–29)-NH$_2$ was obtained. The product was shown to be homogeneous by analytical HPLC. Amino acid composition (Hydrolysis: 6NHCl-TGA; 110°; 24 h): Asp, 3.05; Thr, 0.93; Ser, 2.57; Glu, 2.04; Ala, 4.27; Val, 0.99; Met, 0.98; Ile, 1.93; Leu, 4.16; Tyr, 1.98; Phe, 0.97; Lys, 2.00; Arg, 3.08.

EXAMPLE 9

Preparation of [Ala$^{15}$]-hGRF(1–29)-resin

Boc-Arg(Tos)-resin (Bachem; 3.0 g; 0.615 mmol) was charged into the reaction vessel of the Vega 1000 Peptide Synthesizer and solid phase peptide synthesis performed by the symmetric anhydride procedure for a total of 13 cycles to give hGRF(16–29)-resin (4.4 g). A 1 g portion (0.13 mmol) was subjected to 15 more cycles of solid phase synthesis and at the end of the synthesis the Boc-group of the N-terminus amino acid residue was removed (TFA) and the peptide resin, [Ala$^{15}$hGRF(1–29)-resin, was dried to give 1.66 g.

EXAMPLE 10

Preparation, Purification and Characterization of [Ala$^{15}$]hGRF(1–29)-OH

The [Ala$^{15}$]-hGRF(1–29)-resin from Example 9 (1.66 g) was treated with anhydrous HF, as in example 3, and 262 mg of crude [Ala$^{15}$]hGRF(1–29)-OH was obtained. The crude material was dissolved in 4 mL of 0.1% TFA (H$_2$O), filtered and loaded onto a Nucleosil C18 column (1×50 cm). The column was eluted (3 mL/min) with a solvent system consisting of CH$_3$CN (containing 0.1% TFA) and H$_2$O (containing 0.1% TFA) in a linear gradient mode from 20 to 40% CH$_3$CN in 180 min. Fractions (2 min) were collected and analyzed by analytical HPLC. The desired product emerging in fraction 76 was evaporated and lyophilized, yield: 2.4 mg of [Ala$^{15}$]hGRF-(1–29)-OH which was shown to be homogeneous by analytical hplc. Amino acid analysis (Hydrolysis: 6N HCl-thioglycolic acid; 110°; 24 h): Asp, 2.98; Thr, 0.97; Ser, 2.88; Glu, 2.15; Leu, 3.85; Tyr, 1.93; Arg, 2.95. (Hydrolysis: 6N HCl-TGA; 110°; 72 h): Ala, 4.17; Val 0.99; Met, 1.04; Ile, 1.91; Phe, 0.86; Lys, 2.02.

EXAMPLE 11

Preparation of [Leu$^{15}$]-hGRF(1–29)-OH

A 1 g portion of hGRF(16–29)-resin (from example 9) was subjected to 15 more cycles of solid phase synthesis as in example 9. Yield: 1.16 g of side-chain protected [Leu$^{15}$]hGRF(1–29)-resin. After anhydrous HF cleavage (as in example 3) and subsequent work-up 388 mg of crude [Leu$^{15}$]hGRF(1–29)-OH was obtained. Purification (HPLC), as in example 10, gave 4.4 mg of semipure [Leu$^{15}$]hGRF(1–29)-OH which was subjected to further purification as in example 6. The desired product emerged in fractions 40-42. Yield: 0.9 mg of [Leu$^{15}$]hGRF(1-29)-OH. The product was shown to be homogeneous by analytical HPLC. Amino Acid Analysis (Hydrolysis: 6N HCL-Thioglycolic acid; 110°; 24 h): Asp, 3.06; Thr, 0.94; Ser, 2.95; Glu, 2.11; Ala, 3.05; Val, 0.99; Met, 0.94; Leu, 5.15; Tyr, 1.81; Arg, 3.02; (Hydroysis: 6N HCL-Thioglycolic Acid; 110°; 72 h): Ile, 2.06; Phe, 0.85; Lys, 2.02;

EXAMPLE 12

Preparation of [Val$^{15}$]hGRF(1-29)-OH

A 1 g portion of hGRF(16-29)-resin (from example 9) was subjected to 15 more cycles of solid phase peptide synthesis as in example 9. Yield: 1.30 g of side-chain protected [Val$^{15}$]-hGRF(1-29)-resin. After cleavage from the resin with anhydrous liquid HF (as in example 3) and work-up 158 mg of crude [Val$^{15}$]-hGRF(1-29)-OH was obtained. Purification (as in example 6) gave 4.6 mg of semi-purified product. This material was purified further as in example 10. The product emerging in fraction 78, was evaporated and lyophilized. Yield: 1.8 mg of [Val$^{15}$]hGRF(1-29)-OH. The product was shown to be homogeneous by analytical HPLC: Amino acid analysis Hydrolysis: (6M HCl-Thioglycolic acid; 110°; 72 h): Asp, 2.92; Glu, 200; Ala, 2.91; Val, 2.03; Met, 0.98; Phe, 0.87; Lys, 2.13; Leu, 4.14 Arg, 3.08 (Hydrolysis: 6M HCL-Thioglycolic acid; 150°; 1 h): Ile, 1.93; Tyr, 1.91.

EXAMPLE 13

Synthesis of Boc-Leu-MBHA-resin

Boc-Leu-MBHA-resin was prepared by coupling Boc-Leu-OH (17.68 g, 83 mmol) to methylbenzhydryl amine resin (70 g, 0.28 meq/g) as in example 1. Yield: 72.87 g. Amino acid analysis showed a substitution of 0.23 mmole/g-resin.

EXAMPLE 14

Preparation of [Ala$^{15}$]-hGRF(1-44)methyl benzhydrylamine-resin

Boc-Leu-BHA-resin, from Example 13, (78.87 g, 18.1 mmol) was charged into the reaction vessel of the Vega 296 Peptide Synthesizer and solid phase synthesis performed for a total of 16 cycles to give hGRF(28-44)-MBHA-resin (37.65 g). A 5 g (0.75 mmol) portion was removed and subjected to 12 more cycles of solid phase synthesis to give hGRF(16-44)-MBHA-resin (5.15 g). A 1.7 g portion of this material was subjected to 15 more cycles of solid phase synthesis. At the end of the synthesis the Boc-group of the N-terminal amino acid residue was removed (TFA) and the peptide-resin, [Ala$^{15}$]-hGRF(1-44)-MBHA-resin was dried to give 1.73 g.

EXAMPLE 15

Preparation of [Ala$^{15}$]-hGRF(1-44)-NH$_2$

The [Ala$^{15}$]-hGRF(1-44)-MBHA-resin, of example 14, (0.85 g) was treated with anhydrous liquid HF as in example 3 yield: 380 mg of crude [Ala$^{15}$]-hGRF(1-44)-NH$_2$. A 190 mg portion was subjected to purification as in example 6 (linear gradient 15-35%). The desired product emerged in fractions 42-43 which were combined, evaporated and lyophilized yield: 10.5 mg of [Ala$^{15}$]-hGRF(1-44)-NH$_2$. The product was shown to be homogeneous by analytical hplc. Amino acid composition (Hydrolysis 6NHCl-TGA; 110°; 24 h): Asp, 4.00; Thr, 0.91; Ser, 3.69; Glu, 7.40; Gly, 2.16; Ala, 6.00; Val, 0.97; Met, 0.93; Ile, 1.85; Leu, 5.25; Tyr, 1.83; Phe, 0.85; Lys, 1.97; Arg, 6.16. (Hydrolysis: 6NHCl-TGA; 110°; 72 h): Phe, 0.91.

EXAMPLE 16

Synthesis of [Leu$^{15}$]-hGRF(1-44)-NH$_2$

A 1.79 g portion of hGRF(16-44)MBHA-resin from example 14 was subjected to 15 more cycles of solid phase synthesis as in example 14. Yield: 1.67 g of side-chain protected [Leu$^{15}$]-hGRF(1-44)-MBHA-resin. One half of this material, (835 mg) was treated with anhydrous liquid HF as in example 3. Yield: 400 mg. of crude [Leu$^{15}$]GRF(1-44)-NH$_2$. A 200 mg was subjected to HPLC purification as in examples 6 and 15. The desired product emerged in fractions 43 and 44 which were combined, evaporated and lyophilized. Yield: 11.0 mg of [Leu$^{15}$]hGRF(1-44)-NH$_2$. The product was shown to be homogeneous by analytical HPLC. Amino acid composition (Hydrolysis: 6N HCl-TGA; 110°; 24 H), Asp, 3.89; Thr, 0.93; Ser, 3.67; Glu, 7.40; Gly, 2.15; Ala, 5.00; Val, 0.95; Met, 0.98. (Hydrolysis: 6N HCl-TGA; 110°; 72 h): Phe, 1.02.

EXAMPLE 17

Preparation of [Ala$^{15}$]-GRF(1-38)-NH$_2$

Boc-Arg(Tos)-BHA-resin, as prepared in Example 1, can be charged into the reaction vessel of a Vega 250 Peptide Synthesizer and solid phase synthesis can be performed by the symmetric anhydride procedure for a total of 16 cycles to give GRF(22-38)-BHA-resin. A portion can be removed and subjected to 6 more cycles of solid phase synthesis to give (16-38)-BHA-resin. A portion can then be converted by solid phase synthesis for the remaining 15 cycles. At the end of the synthesis the Boc-group of the N-terminal amino acid residue can be removed using TFA and the peptide resin [Ala$^{15}$]GRF(1-38)-BHA-resin can be dried.

EXAMPLE 18

Preparation, purification and characterization of [Ala$^{15}$]GRF(1-38)-NH$_2$ The [Ala$^{15}$]GRF(1-38)benzhydrylamine-resin, as can be prepared in example 17, can be be treated with anhydrous liquid HF as in example 3. A portion can then be subjected to purification as in Example 6 (linear gradient 15-35%). The desired product emerges in fractions from the column which are combined, evaporated and lyophilized. The product can then be evaluated for homogeneity by analytical HPLC and confirmed by amino acid analysis.

EXAMPLE 19

Synthesis of [Leu$^{15}$]GRF(1-38)-NH$_2$

A portion of GRF(16-38)MBHA-resin from Example 17 can be subjected to 15 more cycles of solid phase synthesis as in Example 17. Protected [Leu$^{15}$]GRF-(1-38)-MBHA resin can be obtained. A portion of the material can be treated with anhydrous liquid HF as in Example 3 to yield crude [Leu$^{15}$]GRF(1-38)NH$_2$. A portion of this crude product can then be subjected to HPLC purification as in Examples 6 and 15. The desired product emerging in several fractions can be combined, evaporated and lyophilized. The product can be shown to be homogeneous by analytical HPLC and confirmed by amino acid analysis.

EXAMPLE 20

Synthesis of [Ala$^{15}$,Leu$^{27}$[GRF(1-29)NH$_2$

The Boc-Arg-(Tos)-BHA resin as prepared in example 1, can be charged into the reaction vessel of a Vega 250 Peptide Synthesizer and solid phase synthesis performed by the symmetric anhydride procedure for a total of 2 cycles to give GRF(28-29)-BHA-resin. A portion can be removed and coupled with Boc-Leu and then subjected to 10 more cycles of solid phase synthesis to give [Leu$^{27}$]GRF(16-29)-BHA-resin. A portion can then be removed and coupled with Boc-Ala and subjected to the remaining 14 cycles of solid phase synthesis as described in Example 3.

EXAMPLE 21

The biological activity of the claimed compounds were compared with that of synthetic GRF(1-44)-NH$_2$ which is comparable to the natural GRF(1-44)NH$_2$. Biological activity of the synthetic GRF(1-44)NH$_2$ was identical to the natural GRF(1-44)NH$_2$ which was isolated from a human pancreatic tumor of an individual suffering from acrommegaly (Salk Institute standard hGRF-NH$_2$(NL-A-10)). The assay for biological activity, which is based on the ability to stimulate production of growth hormone in rat pituitary cells in tissue culture, was performed in the following manner.

Pituitaries from 30-40 male Sprague-Dawley rats (175 g) were removed aseptically after decapitation. The anterior lobes were collected, washed 3 times in sterile Hepes buffer (0.025M) (pH 7.35) and dispersed at 37° C. in 20-30 ml Hepes buffer (pH 7.35) containing collagenase (4 mg per ml) and Dispase (Protease grade II, 2 mg per ml). After gentle 100-110-min. vortexing and trituration by Pasteur pipette, the dispersed cells were separated by centrifugation (150×g, 4 min) and re-suspended in Hepes buffer containing neuraminidase (8 g/ml), and 200 g/ml ethylenediaminetetraacetic acid (EDTA) disodium salt pH 7.35, for 10 min. The cells were washed twice with plating medium and plated on multiwell-plates (1.5 × 10$^5$ cells per ml) using the following defined medium: F-12/DMEM/BGJ (6:3:1) (Gibco: 430-1700/430-1600/320-2591) with 2 g BSA/1., 2.38 g Hepes/1.50 mg PSN antibiotic mixture (Gibco Laboratories), 10 mg/l transferrin (Sigma T2252) with 1.83 gm NazHCO$_3$/l (Baker 3506). The medium in each well was supplemented either with a sample of the novel GRF peptide or natural GRF(1-44)-NH$_2$ at concentrations ranging from 0.8 to 200 fmol. per ml. of medium. Control wells contained no supplement. Plating was done with this medium added with 2% fetal calf serum to ensure rapid fixation of the cells. On the fourth day the cells were washed twice with the defined medium without fetal calf serum. Finally 900 μl of defined medium was added to each well plus 100 μl of the same medium containing each individual treatment, in triplicate. After 4 hours of incubation the medium was collected and diluted as required to conduct radioimmunoassay (RIAs) for rat growth hormone. RIAs for rat growth hormone were conducted using Sinha's anti-murine GH immune serum and procedures according to the National Pituitary Agency using protein A to precipitate antibody antigen complex.

The results of the assays were that the novel (Ala$^{15}$)GRF(1-29)NH$_2$ was compared to GRF(1-29)NH$_2$ and found to be 5.1 times more potent than the unsubstituted shortened GRF. The (Ala$^{15}$)-GRF(1-29)NH$_2$, one of the novel peptides of the instant invention, was also compared to GRF(1-44)NH$_2$ and found to be 4.1 times more potent on a weight for weight basis.

EXAMPLE 22

Preparation of [β-Ala$^{15}$]hGRF(1-29)-NH$_2$

A 1.68 g portion of hGRF(16-29)BHA-resin (1.68 g, 0.30 mmol) from example 6, was subjected to 15 cycles of solid phase peptide synthesis, treated with TFA and dried to yield 1.93 g of side chain protected [β-Ala$^{15}$]hGRF(1-29) BHA-resin. The protected peptide resin was subjected to anhydrous HF cleavage (as in example 3) and after the usual work-up gave 1.2 g of crude [β-Ala$^{15}$]-hGRF(1-29)-NH$_2$. A 200 mg portion [0.05 mmole (theoryl)] was subjected to HPLC purification (as in example 6) and 35.5 mg (0.01 mmoles, 20% yield of [β-Ala$^{15}$]-hGRF(1-29)-NH$_2$ was obtained. The product was shown to be homogeneous by analytical HPLC. Amino acid composition (Hydrolysis: 6N HCl-thioglycolic acid; 150°; 1 h): Asp, 3.13; Thr, 0.98; Ser, 2.95; Glu, 2.14; Ala, 3.13; Met, 1.01; Thr, 2.03; Lys, 1.99. (Hydrolysis: 6N HCl-thioglycolic acid; 110°; 24 h): Val, 1.09; Phe, 1.10; β-Ala, 0.87; Arg, 2.94.

EXAMPLE 23

Preparation of [desNH$_2$Tyr$^1$]hGRF(1-29)-NH$_2$

Protected GRF(3-29)-BHA-resin (1.0 g, 0.13 mmol) as prepared in example 8 was subjected to 2 cycles of solid phase peptide synthesis to give 1.26 g of [desNH$_2$-Tyr$^1$]GRF(1-29)-BHA-resin. Cleavage from the resin with HF, as in example 3 gave 0.79 g of crude [desNH$_2$-Tyr$^1$]GRF(1-29)-NH$_2$.

A 120 mg portion was subjected to HPLC purification, as in example 6, yielding 19.5 mg (30% yield) of [des NH$_2$Tyr$^1$]-hGRF(1-29)-NH$_2$. The product was shown to be homogeneous by analytical HPLC. Amino acid analysis (hydrolysis: 6N HCl-thioglycolic acid; 110°; 24 h): Asp, 3.08; Thr, 0.98; Ser, 2.94; Glu, 2.13; Gly, 1.10; Ala, 3.31; Val, 1.01; Met, 1.01; Ile, 1.97; Leu, 4.29; Tyr, 1.04; Phe, 0.98; Lys, 1.99; Arg, 3.15.

EXAMPLE 24

Preparation of [desNH$_2$-Tyr$^1$,D-Ala$^2$,Ala$^{15}$]hGRF(1-29)-NH$_2$

A portion of hGRF(16-29)-BHA-resin (3.23 g, 0.58 mmol) from example 6, was subjected to 13 cycles of solid phase peptide synthesis, treated with TFA and dried to give [Ala$^{15}$]GRF-(3-29)-BHA-resin. A 1.798 g portion of the protected peptide resin was subjected to 2 cycles of solid phase peptide synthesis in which D-Ala and 3-(4-hydroxyphenyl)propionate were successively added. The protected peptide resin (1.85 g) was treated with HF, as in example 3, and the crude product dried to give 0.827 g. A portion (200 mg) was subjected to HPLC purification, as in example 6, to give [desNH$_2$-Tyr$^1$,D-Ala$^2$,Ala$^{15}$]-hGRF(1-29)-NH$_2$ (22.2 mg; yield: 9%). The product was homogeneous by analytical HPLC. Amino acid composition (Hydrolysis: 6N HCl-thioglycolic acid; 110°; 24 h): Thr, 1.02; Ser, 2.798; Tyr, 1.00; Lys, 2.04; Arg. 3.13; (72 h): Asp, 2.80; Glu, 2.10; Ala, 3.98; Val, 1.04; Met, 1.03; Ile 1.85; Phe, 0.92.

EXAMPLE 25

Preparation of [desNH$_2$Tyr$^1$,Ala$^{15}$]hGRF(1-29)-NH$_2$

A 1.8 g portion of [Ala$^{15}$]hGRF(3-29)-BHA-resin from example 24 was subjected to 2 cycles of peptide synthesis in which Ala and 3-(4-hydroxyphenyl)propionate were successively added. The protected peptide resin was cleaved with HF as in example 3 to give 0.79 g of crude peptide. A portion (200 mg) was subjected to HPLC purification, as in example 6, to give 13 mg (5% yield) of [desNH$_2$Tyr$^1$,Ala$^{15}$]-hGRF(1-29)-NH$_2$. The product was shown to be homogeneous by analytical HPLC. Amino acid composition (Hydrolysis: 6N HCl-thioglycolic acid; 150°; 1 h): Asp, 3.00; Thr, 1.00; Ser, 3.00; Tyr, 0.99; Lys, 1.99; Arg, 3.04; (72 h): Glu, 2.05; Ala, 4.25; Val, 0.99; Met, 0.92; Ile, 1.85; Leu, 3.97; Phe, 0.94.

EXAMPLE 26

Preparation of [α-Aib$^{15}$]hGRF(1-29)-NH$_2$

A portion of hGRF(16-29)BHA-resin (1.68 g, 0.30 mmol) from example 6 was subjected to 15 cycles of solid phase peptide synthesis, treated with TFA and dried to yield 1.93 g of side chain protected [α-Aib$^{15}$]hGRF(1-29)BHA-resin. The protected peptide resin was subjected to anhydrous HF cleavage, as in example 3 and after the usual work-up gave crude [α-Aib$^{15}$]hGRF(1-29)-NH$_2$. A 200 mg portion, approximately 0.05 mmol, was subjected to HPLC purification, as in example 6 and [α-Aib]hGRF(1-29)-NH$_2$ was obtained. The product was shown to be homogeneous by analytical HPLC.

We claim:

1. A growth hormone releasing factor (GRF) compound of the formula $$\text{R}-\text{R}_2-\text{Asp}-\text{Ala}-\text{Ile}-\text{Phe}-\text{Thr}-\text{Asn}-\text{Ser}-\text{Tyr}$$
$$\text{Arg}-\text{R}_3-\text{Val}-\text{Leu}-\text{R}_4-\text{Gln}-\text{Leu}-\text{Ser}-\text{Ala}-\text{Arg}$$
$$\text{Lys}-\text{Leu}-\text{Leu}-\text{Gln}-\text{Asp}-\text{Ile}-\text{R}_5-\text{Ser}-\text{R}_6-\text{X}$$

wherein R represents Tyr, D-Tyr, desNH$_2$-Tyr, Ac-Tyr or His; R$_2$ represents Ala N-Methyl-D-Ala or D-Ala; R$_3$ represents Lys or Ala; R$_4$ represents Ala, Leu, Val, Ile, Nle, Nval, β-Ala or α-Aib; R$_5$ represents Met, Leu, Nle or Ile; R$_6$ represents an amino acid sequence selected from Arg-Gly-Gln-Gly-Glu-Ser-Asn-Gln-Glu-Arg-Gly-Ala-Arg-Ala-Arg-Leu or fragments thereof where the fragment is reduced in number by one to fifteen amino acids from the carboxyl end; and, X is either OH or NH$_2$ and, the pharmaceutically acceptable acid or base addition salts thereof.

2. The compound of claim 1 wherein R$_6$ has the indicated amino acid sequence of fourteen amino acids:

$$\text{R}-\text{R}_2-\text{Asp}-\text{Ala}-\text{Ile}-\text{Phe}-\text{Thr}-\text{Asn}-\text{Ser}-\text{Tyr}$$
$$\text{Arg}-\text{R}_3-\text{Val}-\text{Leu}-\text{R}_4-\text{Gln}-\text{Leu}-\text{Ser}-\text{Ala}-\text{Arg}$$
$$\text{Lys}-\text{Leu}-\text{Leu}-\text{Gln}-\text{Asp}-\text{Ile}-\text{R}_5-\text{Ser}-\text{Arg}-\text{Gln}-\text{Gln}-$$
$$\text{Gly}-\text{Glu}-\text{Ser}-\text{Asn}-\text{Gln}-\text{Glu}-\text{Arg}-\text{Gly}-\text{Ala}-$$
$$-\text{Arg}-\text{Ala}-\text{Arg}-\text{Leu}-\text{X}$$

wherein R, R$_2$, R$_3$, R$_4$ and R$_5$ and X is as in claim 1.

3. The compound of claim 2 which is

[Ala$^{15}$]GRF(1-44)NH$_2$.

4. The compound of claim 2 which is

[Val$^{15}$]GRF(1-44)NH$_2$.

5. The compound of claim 2 which is

[Leu$^{15}$]GRF(1-44)NH$_2$.

6. The compound of claim 1 wherein R$_6$ is one amino acid, Arg, and R, R$_2$, R$_3$, R$_4$, R$_5$ and X are as in claim 1.

7. The compound of claim 6 which is

[Leu$^{15}$]GRF(1-29)NH$_2$.

8. The compound of claim 6 which is

[Val$^{15}$]GRF(1-29)NH$_2$.

9. The compound of claim 6 which is

[Leu$^{15}$]GRF(1-29)OH.

10. The compound of claim 6 which is

[Val$^{15}$]GRF(1-29)OH.

11. The compound of claim 6 which is

[β-Ala$^{15}$]GRF(1-29)NH$_2$.

12. The compound of claim 6 which is

[α-Aib$^{15}$]GRF(1-29)NH$_2$.

13. The compound of claim 1 wherein R$_4$ is alanine and R, R$_2$, R$_3$, R$_5$, R$_6$ and X are as in claim 1.

14. The compound of claim 13 which is

[Ala$^{15}$]GRF(1-29)NH$_2$.

15. The compound of claim 13 which is

[Ala$^{12}$,Ala$^{15}$]GRF(1-29)NH$_2$.

16. The compound of claim 13 which is

[D-Ala$^2$,Ala$^{15}$]GRF(1-29)NH$_2$.

17. The compound of claim 13 which is

[Ala$^{15}$]GRF(1-29)OH.

18. The compound of claim 13 which is

[desNH$_2$Tyr$^1$,Ala$^{15}$]GRF(1-29)NH$_2$.

19. The compound of claim 13 which is

[D-Tyr$^1$,Ala$^{15}$]GRF(1-29)NH$_2$.

20. The compound of claim 13 which is

[Ac-Tyr$^1$,Ala$^{15}$]GRF(1-29)NH$_2$.

21. The compound of claim 13 which is

[desNH$_2$Tyr$^1$,D-Ala$^2$,Ala$^{15}$]GRF(1-29)NH$_2$.

22. The compound of claim 13 which is

[D-Tyr$^1$,D-Ala$^2$,Ala$^{15}$]GRF(1-29)NH$_2$.

23. The compound of claim 13 which is

Ac-[Tyr$^1$,D-Ala$^2$,Ala$^{15}$]GRF(1-29)NH$_2$.

24. The compound of claim 13 which is

[desNH$_2$-Tyr$^1$,D-Ala$^2$,Ala$^{12}$,Ala$^{15}$]GRF(1-29)NH$_2$.

25. The compound of claim 1 wherein R$_4$ is alanine, R$_5$ is leucine, R$_6$ is arginine and R, R$_2$, R$_3$ and X are as in claim 1.

26. The compound of claim 25 which is

[Ala$^{15}$,Leu$^{27}$]GRF(1-29)NH$_2$.

27. The compound of claim 25 which is

[Ala$^{15}$,Leu$^{27}$]GRF(1-29)OH.

28. A pharmaceutical composition for stimulating the release of growth hormone comprising a minor effective amount of the compound of claim 1 and a major amount of a pharmaceutically acceptable liquid or solid carrier.

29. A method of treating growth related disorders characterized by growth hormone deficiencies comprising administering an effective amount of a compound of claim 1 to a subject in need of such treatment.

30. A pharmaceutical composition for stimulating the release of growth hormone comprising a minor effective amount of the compound of claim 2 and a major amount of a pharmaceutically acceptable liquid or solid carrier.

31. A method of treating growth related disorders characterized by growth hormone deficiencies comprising administering an effective amount of a compound of claim 2 to a subject in need of such treatment.

32. A pharmaceutical composition for stimulating the release of growth hormone comprising a minor effective amount of the compound of claim 6 and a major amount of a pharmaceutically acceptable liquid or solid carrier.

33. A method of treating growth related disorders characterized by growth hormone deficiencies comprising administering an effective amount of a compound of claim 6 to a subject in need of such treatment.

34. A pharmaceutical composition for stimulating the release of growth hormone comprising a minor effective amount of the compound of claim 13 and a major amount of a pharmaceutically acceptable liquid or solid carrier.

35. A method of treating growth related disorders characterized by growth hormone deficiencies comprising administering an effective amount of a compound of claim 13 to a subject in need of such treatment.

36. A pharmaceutical composition for stimulating the release of growth hormone comprising a minor effective amount of the compound of claim 25 and a major amount of a pharmaceutically acceptable liquid or solid carrier.

37. A method of treating growth related disorders characterized by growth hormone deficiencies comprising administering an effective amount of a compound of claim 25 to a subject in need of such treatment.

* * * * *

UNITED STATES PATENT AND TRADEMARK OFFICE
CERTIFICATE OF CORRECTION

PATENT NO. : 4,649,131
DATED : March 10, 1987
INVENTOR(S) : ARTHUR M. FELIX, EDGAR P. HEIMER, THOMAS F. MOWLES It is certified that error appears in the above-identified patent and that said Letters Patent are hereby corrected as shown below:

Column 15, line 52, "Arg-Gly-Gln-Gly-Glu-Ser-Asn-Gln-Glu-"

should be:

Arg-Gln-Gln-Gly-Glu-Ser-Asn-Gln-Glu-

Signed and Sealed this

Fourteenth Day of June, 1988

*Attest:*

DONALD J. QUIGG

*Attesting Officer*  *Commissioner of Patents and Trademarks*